United States Patent
Nabatian

(10) Patent No.: US 10,126,298 B2
(45) Date of Patent: Nov. 13, 2018

(54) HYDROGELS CONTAINING EMBEDDED SUBSTRATES FOR TARGETED BINDING OF MOLECULES

(71) Applicant: Arman Nabatian, Morton Grove, IL (US)

(72) Inventor: Arman Nabatian, Morton Grove, IL (US)

(*) Notice: Subject to any disclaimer, the term of this patent is extended or adjusted under 35 U.S.C. 154(b) by 477 days.

(21) Appl. No.: 14/702,893

(22) Filed: May 4, 2015

(65) Prior Publication Data

US 2016/0324985 A1    Nov. 10, 2016

(51) Int. Cl.
| | | |
|---|---|---|
| *G01N 33/543* | (2006.01) | |
| *A61K 47/42* | (2017.01) | |
| *A61K 47/36* | (2006.01) | |
| *A61K 47/34* | (2017.01) | |
| *C07K 16/44* | (2006.01) | |

(52) U.S. Cl.
CPC ......... *G01N 33/5436* (2013.01); *A61K 47/34* (2013.01); *A61K 47/36* (2013.01); *C07K 16/44* (2013.01)

(58) Field of Classification Search
CPC .................................................. G01N 33/5436
See application file for complete search history.

(56) References Cited

U.S. PATENT DOCUMENTS

| | | | |
|---|---|---|---|
| 4,272,518 A | 6/1981 | Moro | |
| 5,292,515 A | 3/1994 | Moro et al. | |
| 5,582,794 A | 12/1996 | Hagiwara et al. | |
| 5,902,798 A | 5/1999 | Gouda et al. | |
| 6,228,393 B1 | 5/2001 | DiCosmo et al. | |
| 6,786,336 B2 | 9/2004 | Boddu et al. | |
| 7,303,814 B2 | 12/2007 | Lamberti et al. | |
| 7,910,135 B2 | 3/2011 | St. John et al. | |
| 8,097,252 B2 | 1/2012 | McBride | |
| 8,703,924 B2 | 4/2014 | Andersson | |
| 8,932,983 B1 | 1/2015 | Harris | |
| 2004/0105834 A1* | 6/2004 | Singh ................... | A61C 19/066 424/70.13 |

OTHER PUBLICATIONS

Annabi, N., S.M. Mithieux, E.A. Boughton, A.J. Ruys, A.S. Weiss, and F. Dehghani. 2009. Synthesis of highly porous crosslinked elastin hydrogels and their interaction with fibroblasts in vitro. Biomaterials. 30:4550-4557.

(Continued)

*Primary Examiner* — Ling Siu Choi
*Assistant Examiner* — Thuy-Ai N Nguyen
(74) *Attorney, Agent, or Firm* — McDonnell Boehnen Hulbert & Berghoff LLP

(57) ABSTRACT

Open three-dimensional network, microporous hydrogels containing substrates attached to binding molecules is disclosed. The hydrogel is comprised of a hydrated gel matrix containing substrates embedded in the matrix. The substrates are attached to binding molecules that selectively bind specific molecules that encounter the hydrogel. Thus the hydrogel serves to selectively bind out target molecules from an aqueous environment or sample that the hydrogel comes in contact with and concentrates them within the hydrogel.

14 Claims, 3 Drawing Sheets

(56) References Cited

OTHER PUBLICATIONS

Annabi, N., S.M. Mithieux, P. Zorlutuna, G. Camci-Unal, A.S. Weiss, and A. Khademhosseini. 2013. Engineered cell-laden human protein-based elastomer. Biomaterials. 34:5496-5505.

Annabi, N., J.W. Nichol, X. Zhong, C. Ji, S. Koshy, A. Khademhosseini, and F. Dehghani. 2010. Controlling the porosity and microarchitecture of hydrogels for tissue engineering. Tissue engineering. Part B, Reviews. 16:371-383.

Annabi, N., A. Tamayol, J.A. Uquillas, M. Akbari, L.E. Bertassoni, C. Cha, G. Camci-Unal, M.R. Dokmeci, N.A. Peppas, and A. Khademhosseini. 2014. 25th anniversary article: Rational design and applications of hydrogels in regenerative medicine. Advanced materials. 26:85-123.

Baruch, L., and M. Machluf. 2006. Alginate-chitosan complex coacervation for cell encapsulation: effect on mechanical properties and on long-term viability. Biopolymers. 82:570-579.

Berger, J., M. Reist, J.M. Mayer, O. Felt, N.A. Peppas, and R. Gurny. 2004. Structure and interactions in covalently and ionically crosslinked chitosan hydrogels for biomedical applications. European journal of pharmaceutics and biopharmaceutics : official journal of Arbeitsgemeinschaft fur Pharmazeutische Verfahrenstechnik e.V. 57:19-34.

Djonlagic, J., D. Zugic, and Z. Petrovic. 2012. High Strength Thermoresponsive Semi-IPN Hydrogels Reinforced with Nanoclays. J Appl Polym Sci. 124:3024-3036.

Gong, J. 2010. Why are double network hydrogels so tough? Soft Matter. 6:2583-2590.

Hahn, M.S., B.A. Teply, M.M. Stevens, S.M. Zeitels, and R. Langer. 2006. Collagen composite hydrogels for vocal fold lamina propria restoration. Biomaterials. 27:1104-1109.

Hague, M., T. Kurokawa, G. Kamita, and J. Gong. 2011. Lamellar bilayers as reversible sacrificial bonds to toughen hydrogel: hysteresis, self-recovery, fatigue resistance, and crack blunting. Macromolecules. 44:8916-8924.

Haraguchi, K., and T. Takehisa. 2002. Nanocomposite hydrogels: a unique organic-inorganic network structure with extraordinary mechanical, optical, and swelling/de-swellingproperties. Adv. Mater. 14:1120-1124.

Hua, S., H. Ma, X. Li, H. Yang, and A. Wang. 2010. pH-sensitive sodium alginate/poly(vinyl alcohol) hydrogel beads prepared by combined Ca2+ crosslinking and freeze-thawing cycles for controlled release of diclofenac sodium. International journal of biological macromolecules. 46:517-523.

Kistler, S. 1931. Coherent expoanded aerogels and jellies. Nature. 127:741.

Leach, J.B., J.B. Wolinsky, P.J. Stone, and J.Y. Wong. 2005. Crosslinked alpha-elastin biomaterials: towards a processable elastin mimetic scaffold. Acta biomaterialia. 1:155-164.

Lee, K.Y., and D.J. Mooney. 2001. Hydrogels for tissue engineering. Chemical reviews. 101:1869-1879.

Li, Y. J. Rodrigues, and H. Tomas. 2012. Injectable and biodegradable hydrogels: gelation, biodegradation and biomedical applications. Chemical Society reviews. 41:2193-2221.

MacEwan, S.R., and A. Chilkoti. 2010. Elastin-like polypeptides: biomedical applications of tunable biopolymers. Biopolymers. 94:60-77.

Myung, D., D. Waters, M. Wiseman, P.E. Duhamel, J. Noolandi, C.N. Ta, and C.W. Frank. 2008. Progress in the development of interpenetrating polymer network hydrogels. Polymers for advanced technologies. 19:647-657.

Okumura, Y., and K. Ito. 2001. The Polyrotaxane Gel: A Topological Gel by Figure-of-Eight Cross-links. Advanced materials. 13:485-487.

Patel, A., A.K. Gaharwar, G. Iviglia, H. Zhang, S. Mukundan, S.M. Mihaila, D. Demarchi, and A. Khademhosseini. 2013. Highly elastomeric poly(glycerol sebacate)-co-poly(ethylene glycol) amphiphilic block copolymers. Biomaterials. 34:3970-3983.

Sawhney, A.S., C.P. Pathak, and J.A. Hubbell. 1993. Interfacial photopolymerization of polyethylene glycol)-based hydrogels upon alginate-poly(l-lysine) microcapsules for enhanced biocompatibility. Biomaterials. 14:1008-1016.

Shi, R., D. Chen, Q. Liu, Y. Wu, X. Xu, L. Zhang, and W. Tian. 2009. Recent advances in synthetic bioelastomers. International journal of molecular sciences. 10:4223-4256.

Sun, J.Y., X. Zhao, W.R. Illeperuma, O. Chaudhuri, K.H. Oh, D.J. Mooney, J.J. Vlassak, and Z. Suo. 2012. Highly stretchable and tough hydrogels. Nature. 489:133-136.

Teng, D. 2012. From chitin to chitosan. In Chitosan-based hydrogels. K. Yao, J. Li, F. Yao, and Y. Yin, editors. CRC Press—Taylor & Francis Group, Boca Ratan, FL. 1-37.

Van Eldijk, M.B., C.L. McGann, K.L. Kiick, and J.C. van Hest. 2012. Elastomeric polypeptides. Topics in current chemistry. 310:71-116.

Wang, Q., J. Zhang, and A. Wang. 2009. Preparation and characterization of a novel pH-sensitive chitosan-g-poly (acrylic acid)/attapulgite/sodium alginate composite hydrogel bead for controlled release of diclofenac sodium. Carbohyd Polym. 78:731-737.

Wang, Y., G.A. Ameer, B.J. Sheppard, and R. Langer. 2002. A tough biodegradable elastomer. Nature biotechnology. 20:602-606.

Kofuju, K., T. Ito, Y. Murata, and S. Kawashima. 2000. The controlled release of a drug from biodegradable chitosan gel beads. Chem. Pharm. Bull. 48:579-581.

Chenite, A. c. Chaput, D. Wang., C. Combes, et al. 2000. Novel injectable neutral solutions of chitosan form biodegradable gels in situ. Biomaterials 21:2155-2161.

Liu, L.-S., S.-Q. Liu, S.Y. Ng, M. Froix, T. Ohno, and J. Heller. 1997. Controlled release of interleukin-2 for tumour immunotherapy using alginate/chitosan porous microspheres. J. Controlled Release 43:65-74.

Berger, J., M. Reist, J.M. Mayer, O. Felt, and R. Gurny. 2004. Structure and interactions in chitosan hydrogels formed by complexation of aggregation for biomedical applications. Eur. J. Pharmaceutics Biopharmaceutics 57:35-52.

Schmidt, J.J., J. Rowley, H. J. Kong. 2008. Hydrogels used for cell-based drug delivery. J. Biomedical Materials Rsrch. Part A 87A:1113-1122.

Yin, Y., and J. Li. "Formation of chitosan-based hydrogels network." In Chitosan-based hydrogels: Functions and applications. Ed. K. Yao, J. Li, F. Yao, Y. Yin. 2011. Boca Rotan, FL: CRC Press, p. 179-233.

* cited by examiner

HYDROGELS CONTAINING EMBEDDED SUBSTRATES FOR TARGETED BINDING OF MOLECULES

STATEMENT REGARDING FEDERALLY SPONSORED RESEARCH

Not applicable.

TECHNICAL FIELD

The present invention relates to hydrogels and more particularly, microporous hydrogels containing a plurality of substrates attached to binding molecules that are embedded in the hydrogel matrices. The embedded substrates with attached binding molecules bind target molecules from aqueous environments or samples that the gels are in contact with and concentrate the target molecules within the hydrogels.

BACKGROUND

Hydrogels are highly hydrated macromolecular networks, dispersed in water or other biological fluids. Hydrogels are used in widespread biomedical applications including drug delivery vehicles, cell encapsulation matrices and tissue engineering scaffolds. Hydrogels are porous and nanostructured materials that exhibit properties such as microporosity, surface area, low density, transparency and low heat conductivity similar to natural tissue. S. Kistler first synthesized hydrogels in the 1930's, e.g. (Kistler, 1931). Kistler fabricated them from a variety of naturally-occurring materials such as cellulose-derivatives.

A hydrogel is a material that absorbs solvents (such as water), undergoes rapid swelling without discernible dissolution, and exhibits a three-dimensional microporous network where solvent is absorbed and capable of flowing through the network. Hydrogels may be uncross-linked or cross-linked. Uncross-linked hydrogels are typically able to absorb water but do not dissolve due to the presence of hydrophobic and hydrophilic regions interacting together. Covalently cross-linked networks of hydrophilic polymers, including water soluble polymers, are traditionally denoted as hydrogels in the hydrated state.

A common use of hydrogels is in soft contact lenses. They are also used as burn and wound dressings to facilitate healing, with and without incorporated drugs that can be released from the gel matrix (DiCosmo and DiTizio, 2001; Moro et al., 1981; St. John and Moro, 2011). Hydrogels are also used as coatings to enhance the wettability of the surfaces of medical devices such as blood filters (Hagiwara et al., 1996). Another example of their use is as devices for the sustained release of biologically active substances. For example, Moro et al. discloses a method of preparing a hydrophilic reservoir drug delivery device (Moro et al., 1994).

There are many applications that require the removal of specific molecules (agents) within an aqueous sample. One example is detecting the presence of molecules—such molecules can be detected by removing them from the sample and determining their presence. Furthermore, such collected molecules can be analyzed or even quantified. Alternatively, in some cases, removing certain molecules from a sample can decrease the interference those molecules may have when detecting or analyzing another molecule of interest. In an analytical diagnostic test, binding out targeted molecules can be a means to both concentrate and collect those molecules for detection or analysis; or, their removal can be a means to remove molecules that interfere with the detection or analysis of another analyte. For example, in a medical diagnostic test, target molecules for detection or analysis can include disease or pathogen markers from a biological sample. In an environmental diagnostic test, the target molecule can involve a pollutant, a toxin, a micro-organism, or associated markers of these from an aqueous sample. An example of a biothreat diagnostic test can involve binding a viral agent, a microbial agent, a biotoxin, or chemical marker from a sample. Medical apparatuses can be used to benefit a patient, including binding biologically active molecules that result from disease, or that have a detrimental effect on health and patient healing. An example of a research tool would include the binding of diluted biological or chemical molecules from a reaction, test solution or research organism.

Current methods for binding out agents and concentrating them rely heavily on mechanical action whereby a sample is introduced with binding molecules such as antibodies or aptamers, allowed time to mix in order to enable dispersion of the binding molecules and, following recognition and binding of target molecules, the use of centrifugation, gravity or magnetic fields to separate the complexed binding molecules from the starting material for detection or analysis.

SUMMARY OF INVENTION

In a first aspect, the invention is directed to a hydrogel comprising an organic polymer, wherein embedded within the hydrogel is a plurality of substrates, and wherein the substrate comprises at least one binding molecule. In such hydrogels, the organic polymer can comprise chitosan, and further comprise poly(ethylenimine). In chitosan-poly(ethylenimine) hydrogels, the chitosan may be present at about 0.45% (w/v) to about 2.4% (w/v), while the poly(ethylenimine) may be present at about 0.5% (v/v) to about 3.3% (v/v). In some hydrogels, the chitosan is present at about 0.8% (w/v), and the poly(ethylenimine) is present at about 2%. In some hydrogels comprising chitosan, the organic polymer can further comprise poly(ethylene oxide). In such chitosan-poly(ethylene oxide) hydrogels, the chitosan may be present at about 0.5% (w/v) to about 2.5% (w/v), and the poly(ethylene oxide) at about 0.5% (w/v) to about 2.5% (w/v); including about 0.75%. In yet other chitosan hydrogels, the organic polymer can further comprise glycerol phosphate. In such chitosan-glycerol phosphate hydrogels, the chitosan can be present to a maximum of about 1.8% (w/v), while the glycerol phosphate can be present at about 10% (w/v) to about 30% (w/v). In some chitosan-glycerol phosphate hydrogels, the chitosan is present at about 0.8% (w/v), and the glycerol phosphate is present at about 20% (w/v). In yet other hydrogels, the organic polymer comprises agarose, which can be present at about 0.25% (w/v) to about 2.5% (w/v); in some agarose gels, the agarose is present at about 0.5% (w/v). In other hydrogels, the organic polymer comprises alginate, which can be present at about 1% (w/v) to about 6% (w/v), such as 4%. Alginate gels can be in the presence of a divalent cation, such as $Ca^{2+}$ or $Mg^{2+}$. In all such hydrogels, the substrate can be one selected from the group consisting of agarose, cross-linked agarose, cellulose, dextran, polyacrylamide, latex, polystyrene, polyethylene, polypropylene, polyfluoroethylene, polyethyleneoxy, glass, silica, controlled pore glass, reverse phase silica, and metal. In some cases, the substrate comprises polystyrene. When the substrate is spherical, it can have a diameter of about 20 nm to 500 µm, such as 800 nm. The substrate can be present at about 0.01% (w/v) to about 1% (w/v), such as 0.2% to about 0.5%. The substrates may further comprise a binding molecule, which binding molecule can be selected from the group consisting of a binding polypeptide, a binding polynucleotide, a sugar, a binding polypeptide that binds at least one antigen, an antibody, an antibody fragment, an scFv molecule, an major histocompatibility complex molecule, and an aptamer. The binding molecule can bind an organic or inorganic molecule. An example of a bound organic molecule is a polypeptide. In some cases, the binding molecule binds a cell, a virus, or a viral particle. The bound cell can be a prokaryote or a eukaryote.

In another aspect, the invention is directed to methods of detecting an agent or analyst, comprising (a) contacting a sample with any of the previously described hydrogels comprising a substrate comprising a binding molecule, where the binding molecule binds an agent; (b) allowing the binding molecule to bind the agent; and (c) analyzing the hydrogel for the presence of the agent. The method can further comprise quantifying the agent. The agent can be an organic or inorganic molecule. In the case of an organic molecule, it can comprise a disease marker or a biologically active molecule. The agent itself can comprise a cell, a virus, or a viral particle. The binding molecule can bind a cell, wherein the cell is a prokaryote or a eukaryote.

In a third aspect, the invention is directed to methods of detecting a disease or disorder, comprising (a) providing a sample from a subject suspected of suffering from a disease or disorder; (b) contacting the sample with any of the previously described hydrogels comprising a substrate comprising a binding molecule, wherein the binding molecule binds a molecule correlated with the presence of the disease or disorder; and (c) detecting from the hydrogel the presence of the bound molecule. The method can further include quantifying the bound molecule.

In a fourth aspect, the invention is directed to methods of removing an agent from a sample, comprising (a) contacting a sample with any of the previously described hydrogels comprising a substrate comprising a binding molecule wherein the binding molecule binds an agent; (b) allowing the binding molecule to bind the agent; and (c) removing the hydrogel from the sample, wherein removing the hydrogel results in removing at least a quantity of the agent from the sample.

In a fifth aspect, the invention is directed to methods of treating a tumor cell, comprising placing in proximity to, or contacting, the tumor cell with any of the previously described hydrogels comprising a substrate comprising a binding molecule, wherein the binding molecule binds a tumor-promoting factor. The tumor-promoting factor can comprise one selected from the group consisting of transforming growth factor β, vascular endothelial growth factor A, vascular endothelial growth factor C, chemokine ligand 12, Interleukin 1, Interleukin 8, Interleukin 10, Interleukin 17, TIMP metallopeptidase inhibitor 2, fibroblast activation protein-α, chemokine ligand 17, chemokine ligand 21, hepatocyte growth factor, epidermal growth factor, basic fibroblast growth factor, B-cell lymphoma 2, interferon α, natural killer group 2 ligands, and a member D receptor. The tumor cell can be in vivo.

In yet a sixth aspect, the invention is direct to methods of treating a wound or tissue trauma with any of the previously described hydrogels comprising a substrate comprising a binding molecule, wherein the binding molecule binds a healing-deterring factor. The healing-deterring factor can be selected from the group consisting of natural killer group 2 ligands, member D, transforming growth factor α, transforming growth factor β, interleukin 1, interleukin 6, interleukin 8, fibroblast growth factor 2, fibroblast growth factor 7, fibroblast growth factor 10, platelet derived growth factor, tumor necrosis factor α, chemokine ligand 10, interferon γ, and angiostatin.

In a seventh aspect, the invention is directed to kits, the kits comprising instructions and components of a hydrogel and a plurality of substrates comprising a binding molecule to be embedded therein, and at least one solvent, wherein the solvent, components, and substrate are mixed before use. The instructions can be provided on tangible media, electronic storage media, or the web. The components of the hydrogel can comprise chitosan, and further comprise, for example poly(ethylenimine), poly(ethylene oxide), and glycerol phosphate. In the case of chitosan-poly(ethylenimine) hydrogels, the poly(ethylenimine) can be present at about 0.5% (v/v) to about 3.3% (v/v) and the chitosan can be present at about 0.5% (w/v) to about 2.4% (w/v) when mixed with a solvent; in some such gels, the poly(ethylenimine) is present at about 2% (v/v) and the chitosan is present at about 0.8% (w/v) when the hydrogel is mixed with the solvent. For chitosan-poly(ethylene oxide) hydrogels, the chitosan may be present at about 0.5% (w/v) to about 2.5% (w/v), and the poly(ethylene oxide) at about 0.5% (w/v) to about 2.5% (w/v); including about 0.75% when the hydrogel is mixed with the solvent. In chitosan-glycerol phosphate hydrogels, the chitosan can be present to a maximum of about 1.8% (w/v), while the glycerol phosphate can be present at about 10% (w/v) to about 30% (w/v) when mixed with the solvent. In some chitosan-glycerol phosphate hydrogels, the chitosan is present at about 0.8% (w/v), and the glycerol phosphate is present at about 20% (w/v) when mixed with the solvent. Alternatively, the hydrogel can comprise alginate, wherein the alginate can be present at about 1% (w/v) to about 6% (w/v) in the solvent. The alginate can further comprise a divalent cation, such as $Ca^{2+}$ or $Mg^{2+}$. The solvent, in any case, can be water, saline, or phosphate buffered saline. The binding molecule can bind an organic molecule or an inorganic molecule. In the case of an organic molecule, the organic molecule can be a polypeptide. The binding molecule can also bind a cell, a virus, or a virus particle. In the case of a cell, the cell can be a prokaryote or a eukaryote. The binding molecule can bind a molecule correlated with the presence of a disease or disorder. The binding molecule can also bind a tumor-promoting factor, such as one selected from the group consisting of transforming growth factor β, vascular endothelial growth factor A, vascular endothelial growth factor C, chemokine ligand 12, Interleukin 1, Interleukin 8, Interleukin 10, Interleukin 17, TIMP metallopeptidase inhibitor 2, fibroblast activation protein-α, chemokine ligand 17, chemokine ligand 21, hepatocyte growth factor, epidermal growth factor, basic fibroblast growth factor, B-cell lymphoma 2, interferon α, natural killer group 2 ligands, and a member D receptor. The binding molecule can also bind a healing-deterring factor, such as one selected from the group consisting of natural killer group 2 ligands, member D, transforming growth factor α, transforming growth factor β, interleukin 1, interleukin 6, interleukin 8, fibroblast growth factor 2, fibroblast growth factor 7, fibroblast growth factor 10, platelet derived growth factor, tumor necrosis factor α, chemokine ligand 10, interferon γ, and angiostatin.

BRIEF DESCRIPTION OF THE DRAWINGS

FIG. 3A shows a hydrogel under normal lighting conditions comprising beads coated with anti-FITC antibodies and briefly incubated with FITC-labelled streptavidin protein prior to imaging. FIG. 3B shows the same hydrogel under 488 nm light, exciting the FITC molecules, and the fluorescence photographed at 518 nm, demonstrating that the fluorescent signal has concentrated in the hydrogel.

DETAILED DESCRIPTION

Figure 1:
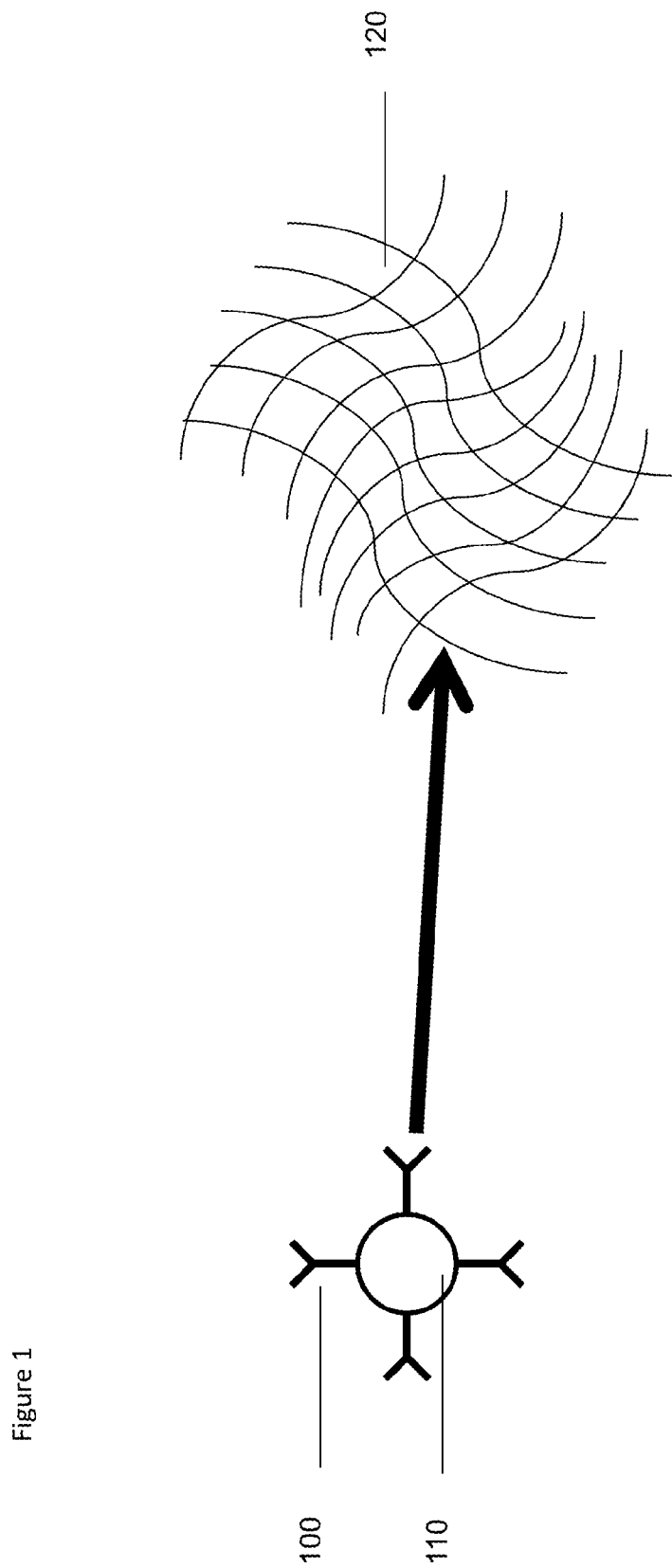
FIG. 1 shows a schematic of hydrogels of the invention. Binding molecules 100, such as antibodies, are attached to a substrate 110 and embedded (arrow) in a hydrogel 120.
Figure 2:
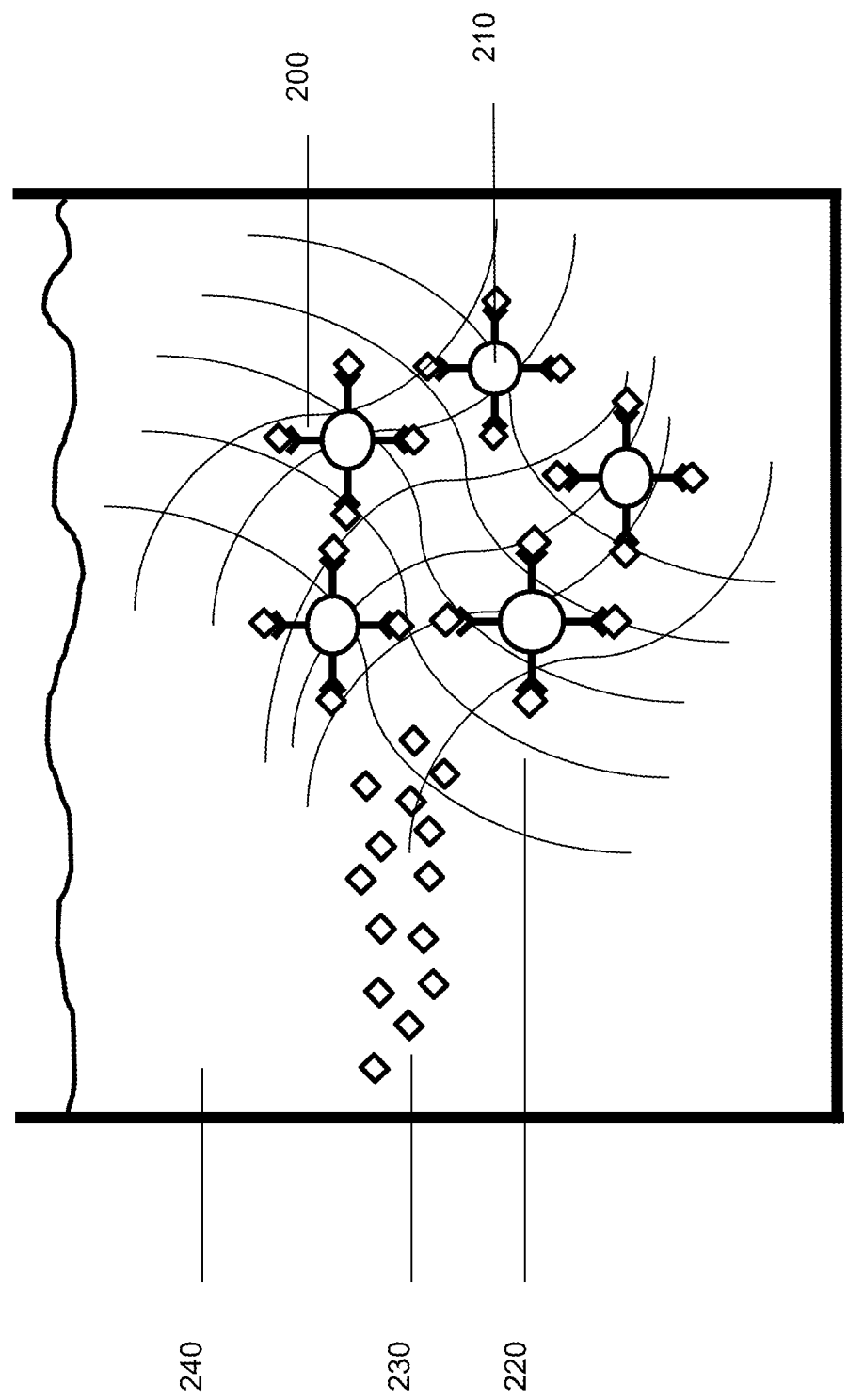
FIG. 2 shows target molecules 230 within a solution 240 entering into a hydrogel matrix 220 in which are embedded binding molecules 200, such as antibodies, that are attached to a substrate 210. The target molecules are bound by the binding molecules in the hydrogel.

In the present invention, hydrogels are embedded with a plurality of substrates attached to binding molecules (FIG. 1). In this way, when the hydrogel is placed in contact with an aqueous environment containing molecules of interest, those target molecules can enter the hydrogel, are bound by the binding molecules attached to the substrates, and their concentrations become enriched over time within the hydrogel compared to the concentration of the same molecules outside of the hydrogel within the sample (FIG. 2). This method does not require mechanical action to separate the binding molecules with bound target molecules from the sample, only removal of the hydrogel from the sample to remove the bound target molecules, if desired. Such hydrogels have diverse applications where "binding out" target molecules from a sample is desired, whether to remove the target molecules from the sample for further analysis of the sample, or for analysis of the bound target molecules. This method differs from those previously described, for example, by Harris and Hajela (Harris and Hajela, 2015) and Boddu and Smith (Boddu and Smith, 2004), who disclose chitosan coated substrates, not a plurality of substrates embedded in a hydrogel.

So that the invention may be more readily understood, certain terms are first defined.

Definitions

"Aptamer" refers to poly-nucleic acid or peptide molecules that bind to specific target molecules including micro- or macromolecules, nucleic acids, peptide molecules, and even cells, tissues and organisms. Aptamers can be engineered by selection from a diverse sequence pool, or through use of natural aptamers such as those that exist in riboswitches. Aptamers can be modified to contain other molecules such as RNA enzymes (ribozymes) capable of performing specific biochemical reactions, including self-cleaving in the presence of their target molecule. Nucleic acid based aptamers consist of strands of oligonucleotides, and peptide aptamers consist of a short variable peptide domain.

An "aqueous environment" is, unless otherwise indicated, a solution containing water from 1 to 100% of volume. The aqueous environment or sample can be from a natural source such as water from rain, a lake, the sea, the ground, rivers, streams or artificial ones such as prepared solutions with known chemistries.

A "biological sample" or "body fluid sample" is, unless otherwise indicated, a solid, or semi-solid sample, including feces, biopsy specimens, skin, nails, and hair; or a liquid sample, such as urine, saliva, sputum, mucous, blood, blood components (such as plasma or serum), amniotic fluid, semen, vaginal secretions, tears, spinal fluid, washings, and other bodily fluids. Included among the sample are swab specimens from, e.g., the cervix, urethra, nostril, and throat.

"Chitosan" is a modified carbohydrate polymer derived from the chitin component of the shells of crustacean, such as crab, shrimp, and cuttlefish. Chitosan is a copolymer of β-[1→4]-linked 2-acetamido-2-deoxy-D-glucopyranose and 2-amino-2-deoxy-D-glucopyranose (Berger et al., 2004). Chitosan can be obtained by alkaline deacetylation of chitin (Berger et al., 2004) or by using chitin deacetylase (Teng, 2012).

"Hydrogel" means a macromolecular network swollen in water or biological fluids.

Hydrogels can be classified into three classes: (1) entangled networks; (2) covalently cross-linked networks; and (3) networks formed by physical interactions. In the case of chitosan-containing gels, these hydrogels can be classified as chemical hydrogels, wherein irreversible covalent links help form the hydrogel; and physical hydrogels, which are formed by reversible links (Berger et al., 2004).

"Nucleoside" refers to a compound comprising a purine, deazapurine, or pyrimidine nucleobase, e.g., adenine, guanine, cytosine, uracil, thymine, 7-deazaadenine, 7-deazaguanosine, and the like, that is linked to a pentose at the 1'-position. When the nucleoside nucleobase is purine or 7-deazapurine, the pentose is attached to the nucleobase at the 9-position of the purine or deazapurine, and when the nucleobase is pyrimidine, the pentose is attached to the nucleobase at the 1-position of the pyrimidine.

"Nucleotide" refers to a phosphate ester of a nucleoside, e.g., a triphosphate ester, wherein the most common site of esterification is the hydroxyl group attached to the C-5 position of the pentose. The term "nucleoside/tide" means a set of compounds that includes both nucleosides and nucleotides.

A "patient" or "subject" is an individual, typically a human, from whom a sample is collected. The patient or subject may also be a non-human animal, particularly a mammal.

Hydrogels

A hydrogel matrix is composed of hydrophilic polymers, such as sugars, nucleosides, proteins, synthetic organic polymers or a mixture of these, including chemically modified versions. The hydrogel requires an aqueous environment or sample for hydration in order to swell, change volume and exhibit intrinsic properties such as its storage modulus, loss modulus, compressive modulus as well as its ability to withstand stress and strain. Any hydrogel that is able to accommodate a substrate and allows diffusion of a target molecule is useful in the invention.

Hydrogels useful in the invention can be derived from natural materials or synthetic materials. For hydrogels that are used in conjunction with analytic samples, bio-incompatible materials can be used; but those that come in contact with a subject are preferably biocompatible; that is, existing on or within the body without damaging adjacent cells or leading to significant scarring, or otherwise elicit a response that detracts from the hydrogel's proposed function (Lee and Mooney, 2001).

Thus any organic polymer that can form a gel that may or may not be biocompatible is useful in the hydrogels of the invention. Examples of hydrogels are given in Table 1, which list types of hydrogels; those examples of hydrogels that are naturally physically linked (such as by H-bonding, ionic interactions, or protein-protein interactions) may also be chemically or photo-cross-linked, provided a suitable cross-linker is provided.

TABLE 1

Examples of hydrogels (adapted from (Annabi et al., 2014))

| Type of hydrogel | Notes | Reference |
| --- | --- | --- |
| "Naturally derived" | Includes collagen, chitosan, hyaluronic acid, alginate, gelatin, elastin chondroitin sulfate, heparin, and composites thereof | (Li et al., 2012) |
| Polyethylene glycol | Controllable degradation and microstructure | (Annabi et al., 2010; Annabi et al., 2014) |
| Poly(vinyl alcohol) | Controllable degradation and microstructure | (Annabi et al., 2010; Annabi et al., 2014) |
| Poly(2-hydroxyethyl methacrylate) | Controllable degradation and microstructure | (Annabi et al., 2010; Annabi et al., 2014) |
| polyacrylamide | Controllable degradation and microstructure | (Annabi et al., 2010; Annabi et al., 2014) |
| Elastomeric materials | Elastin-based, whether naturally derived or recombinantly synthesized. Naturally-derived elastin hydrogels include those made from solubilized elastin ($\alpha$-elastin and K-elastin) | (Annabi et al., 2009; Leach et al., 2005) |
| Methacrylated tropoelastin | Functionalized recombinant elastin with methacrylate groups and UV cross-linking | (Annabi et al., 2013) |
| Elastin-like polypeptides | Tunable degradation rates, similarity to native extracellular matrix | (MacEwan and Chilkoti, 2010; van Eldijk et al., 2012) |
| Poly(glycerol sebacate) | Polycondensation of glycerol and sebacic acid; can be co-polymerized with polyethylene glycol | (Patel et al., 2013; Shi et al., 2009; Wang et al., 2002) |
| Polyurethanes | | (Annabi et al., 2014)) |
| Composite elastomers | Includes nanocomposite hydrogels, polyrotaxane gels, double network gels, hydrophobic bilayers/polyacrylamide composite, and polyacrylamide/alginate composite | ADDIN EN.CITE (Djonlagic et al., 2012; Gong, 2010; Haque et al., 2011; Haraguchi and Takehisa, 2002; Okumura and Ito, 2001; Sun et al., 2012) |
| Polymer composite-including hybrid hydrogels, IPN, and semi-IPN hydrogels, | Mixture of polymers, such as alginate composites which comprise alginate with collagen, fibronectin, polylysine, chitosan, polyvinyl alcohol, and polyacrylic acid. See also chitosan composite gels described further below. | (Baruch and Machluf, 2006; Hahn et al., 2006; Hua et al., 2010; Sawhney et al., 1993; Wang et al., 2009) |
| Hybrid | Co-polymerization that covalently links secondary polymers to hydrogel | (Annabi et al., 2014) |
| IPN/semi-IPN | IPN-interpenetrating polymer network. Have enhanced "toughness"; secondary polymers are placed in formed hydrogels and allowed to polymerize | (Gong, 2010; Myung et al., 2008; Thomas and Sperling, 1978) |
| Nanocomposite | Nanoparticles are incorporated into hydrogels | (Annabi et al., 2014) |

In some embodiments of the invention, hydrogels contain chitosan. Chitosan behavior is influenced by its molecular weight and degree of deacetylation. In some embodiments, chitosan that is 75% or more deactylated is desired, including 75%, 80%, 85%, 90%, 95%, and 100% deactylated.

Chitin may be extracted from a natural source, for example, animal tissue such as squid pens and shrimp shells, vegetable sources such as mushrooms (e.g., "champignon de Paris"), or chitin may be synthesized by modified microorganisms such as bacteria, or the chitin may be synthetically produced.

There is no limitation on the kind of chitosan used in the present invention. Examples of chitosan derivatives include thiolated chitosan, trimethylated chitosan, carboxymethyl chitosan, N-(2-hydroxyl propyl-3-trimethyl ammonium) chitosan chloride and the like. Preferably, the chitosan suitable for the present invention may have an average molecular weight ranging from 3,000 to 1,000,000 daltons, more preferably, 30,000 to 200,000 daltons.

In some embodiments of the invention, chitosan is present at about 0.8% (w/v), also from about 0.45% to about 2.5% (w/v), including about 0.45%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, and about 2.5% (w/v) in the hydrogel. The percentage of chitosan desired depends on in part the size of the pores that are desired. As chitosan and other polymers increase in concentration, the pores grow smaller in size. This ability to tune the pore size enables direct regulation of the size of molecules that enter and leave the hydrogel, as well as regulation of their diffusion rates.

In other embodiments, chitosan is present with another polymer, such as branched polyethylenimine (PEI). Preferably, the PEI polymer has an average molecular weight of about 25,000. In chitosan-PEI hydrogels, PEI can be present at about 2% (v/v), but may be present from 0.5% to 3.3%, (v/v), including about 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.6%, 2.8%, 2.9%, 3.0%, 3.1%, 3.2%, and about 3.3% (v/v).

In preparing chitosan-PEI gels, the chitosan is dissolved in acetic acid, such as 0.5% to 1.5% acetic acid, preferably dissolved in 1% acetic acid (pH=4), and the PEI is prepared in water. Chitosan-PEI gels are not covalently cross-linked.

In other embodiments, chitosan is present with the polymer poly(ethylene oxide) (PEO). In chitosan-PEO gels, PEO can be present at about 0.5% (w/v), but may be present from about 0.25% to about 2.5% (w/v), including 0.25%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, and about 2.5% (w/v).

In yet other embodiments, chitosan is present with glycerol phosphate (GP). In chitosan-GP gels, GP can be present at about 20% (w/v) GP, but may be present from about 10% (w/v) to about 30% (w/v), including 10%, 11%, 12%, 13%, 14%, 15%, 16%, 17%, 18%, 19%, 20%, 21%, 22%, 23%, 24%, 25%, 26%, 27%, 28%, 29%, and about 30% (w/v). In chitosan-GP gels, chitosan does not usually exceed 1.8% (w/v).

In one embodiment, chitosan is present at about 0.8% (w/v), and PEI is present at about 2% (v/v). In another embodiment, chitosan is present at about 0.5% (w/v), and PEO is present at about 0.8%. In another embodiment, chitosan is present at about 0.5% (w/v), and GP is present at about 20% (w/v) GP.

In yet other embodiments, hydrogels are prepared from low-melting point agarose (LMP agarose). LMP agarose can be present in the gels preferably at 0.5% (w/v), but may be present from about 0.25% to about 2.5% (w/v), including about 0.25%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, and about 2.5% (w/v). The LMP agarose is diluted in water or other aqueous solution, such as a buffer, such as phosphate-buffered saline (PBS). The integrity of such gels depends on non-covalent links.

In other embodiments, hydrogels are prepared from alginate and calcium ions. Alginic acid is a linear copolymer with homopolymeric blocks of (1→4)-linked β-D-mannuronate and its C-5 epimer α-L-guluronate residues, respectively, covalently linked together in different sequences. It can be isolated from brown algae. In alginate gels, alginate is present at about 4% (w/v), but may be present from about 1% to about 6% (w/v), including 1%, 1.5%, 2%, 2.5%, 3%, 3.5%, 4%, 4.5%, 5%, 5.5%, and about 6% (w/v). To provide non-covalent links, the alginate is mixed with a cation, such as $Ca^{2+}$, which concentration can vary with the concentration of alginate. In some embodiments, calcium is present in the form of calcium chloride at about 0.8M, including about 0.4M, 0.5M, 0.6M, 0.7M, 0.8M, 0.9M, 1M, 1.5M, and 2M.

In some embodiments, the hydrogels are linked only by intermolecular interactions; in other embodiments, the hydrogels are physically linked, such as by ionic bonds. In other embodiments, the hydrogels are covalently linked.

Hydrogels can be prepared with a variety of aqueous solvents. When intended for in vivo use, it may be desirable to prepare the hydrogels with saline or phosphate buffered saline. In other applications, water is desired; in some instances where cations (e.g., $Ca^{2+}$) or anions provide physical connections in the hydrogel, the solvent can contain these cations or anions.

Substrates

A plurality of substrates, or solid supports, is embedded within the gel; connected to these substrates are binding molecules. The configuration of a substrate can be in the form of beads, spheres, particles, granules, a gel, a membrane, or a surface. Surfaces can be planar, substantially planar, or non-planar. Solid supports can be porous or non-porous.

A support or matrix is any material to which a binding molecule is covalently attached. Typically, the material to be used is insoluble in the hydrogel. Many substances have been described and utilized as matrices, including agarose (such as cross-linked agarose), cellulose, dextran, polyacrylamide, latex, polystyrene, polyethylene, polypropylene, polyfluoroethylene, and polyethyleneoxy, as well as copolymers and grafts thereof. Solid supports can also comprise inorganic materials, such as glass, silica, controlled pore glass (CPG), reverse phase silica; or metal, such as gold, iron (such as iron oxide), or platinum. Especially useful supports are those with a high surface area to volume ratio, chemical groups that are easily modified for covalent attachment of binding molecules, minimal nonspecific binding properties, good flow characteristics, and mechanical and chemical stability.

Methods for immobilizing binding molecules on the substrates are well known in the art, and binding molecules can be attached covalently or non-covalently. In most embodiments, the binding molecule is covalently attached to the support. The types of functionalities generally used for attachment include easily reactive components, such as primary amines, sulfhydryls, aldehydes, carboxylic acids, hydroxyls, phenolic groups, and histidinyl residues. Most often the solid support is first activated with a compound that is reactive to one of these functionalities. The activated complex can then form a covalent linkage between the binding molecule and the support, immobilizing the binding molecule on the solid support.

Coupling binding molecules through their amine groups is possible because of the abundance of lysine side chain ε-amines and N-terminal α-amines. Solid supports are prepared to have free aldehyde groups, which can be used to immobilize amine-containing binding molecules by reductive amination. For example, cyanoborohydride or other appropriate mild reducing agent can be used to couple the binding molecule to an aldehyde-prepared support.

In other amine-reactive methods, solid supports are derivatized with an azlactone ring, such as is available from Life Technologies (Grand Island, N.Y.). Another approach is to prepare supports (such as agarose supports) with reactive imidazole carbamates. This method is also appropriate for immobilizing binding molecules that are small organic molecules. Other amine-reactive methods include the use of N-Hydroxysuccinimide (NHS)-ester-, periodate and cyanoborohydride-, and cyanogen bromide-activated supports.

Coupling through sulfhydryl groups can have the advantage that coupling can occur at distinct (thiol group) sites on the coupled protein instead of the more ubiquitous amine groups. Such coupling may be advantageous to avoid coupling at binding sites in the binding molecules. Binding molecules, especially polypeptides, can be engineered to include a terminal sulfhydryl group to promote coupling. Supports that have been derivatized with iodo-acetyl groups, preferably at the end of a spacer arm are useful for sulfhydryl-mediated coupling.

As with sulfhydryl group coupling, coupling through carbonyl groups can also have the advantage of localized coupling. Although biological molecules do not usually contain carbonyl ketones or aldehydes, such groups can be created. Glycomolecules (e.g., glycoproteins and glycolipids) often have sugar residues that are adjacent to carbon molecules having hydroxyl groups; these can be periodate-oxidized to create aldehydes. These aldehydes can be linked to supports through immobilized hydrazide, hydrazine, or amine group (by Schiff base formation or reductive amination).

Coupling through carboxyl groups is also useful. Supports containing amines or hydrazides can be used to form amide bonds with carboxylates through carbodiimide-mediated reactions, such as those using the carbodiimide, 1-Ethyl-3-(3-dimethylaminopropyl) carbodiimide (EDC).

In some embodiments, the binding molecule can be bound to another molecule that is directly linked to the support. For example, protein A or protein G may be coupled to the support, and then the bound protein used to bind antibodies or other binding proteins comprising a protein A or protein G binding portion. Likewise, avidin- or streptavidin-coated supports can be used for molecules that are biotinylated. Finally, binding molecule polypeptides can be engineered to have "tags" incorporated into the polypeptide, such as a His tag, and then use supports prepared with a molecule that binds the tag, such as nickel.

Many commercial kits are available for coupling, such as those from Life Sciences, InnovaBiosciences (Cambridge, UK), PlexBio (South San Francisco, Calif.), Polysciences, Inc. (Warrington, Pa.), and Bangs Laboratories, Inc. (Fishers, Ind.).

The size of the substrates can vary. For example, spherical supports can be about 20 nm-500 µm in diameter, including about 20 nm, 100 nm, 200 nm, 300 nm, 400 nm, 500 nm, 600 nm, 700 nm, 800 nm, 900 nm, 1,000 nm (1 µm), 2 µm, 3 µm, 4 µm, 5 µm, 10 µm, 50 µm, 100 µm, 150 µm, 200 µm, 250 µm, 300 µm, 350 µm, 400 µm, 450 µm, and about 500 µm. In some embodiments, the support diameter is about 800 nm.

The plurality of substrates can be present in hydrogels at a wide variety of concentrations, so long as the integrity of the hydrogel is not compromised. For example, substrates may be present at 1% (w/v), but may also be present at 0.01% to about 1.0%, including 0.05%, 0.1%, 0.2%, 0.3%, 0.4%, 0.5%, 0.6%, 0.7%, 0.8%, 0.9%, and about 1% (w/v) or even higher concentrations. In one embodiment, the supports are present at about 0.2%. The selected percentage will depend in part on the size of the substrate used, the type of material comprising the substrate, and the density of the binding molecule on the support for an optimal or a desired storage capacity of target within the hydrogel.

Binding Molecules

The selection of the binding molecule to be immobilized on a support depends on the desired target. In some embodiments, the binding molecule is a polypeptide. In other embodiments, the binding molecule is a polypeptide that is an antibody (including monoclonal and polyclonal antibodies), an antibody fragment (Fab, Fab', F(ab')2, half Ig, and Fc), or a polypeptide having antigen-binding capacity (such as scFv, diabodies and other fusion polypeptides), which can be engineered. In other embodiments, the binding molecule is a lipid, such as a glycolipid. In yet other embodiments, the binding molecule is a glycoprotein, such as a cell receptor or microbial coat protein. In yet other embodiments, the binding molecule is an aptamer.

"Antibody" (Ab) comprises Abs directed against a desired target, Ab compositions with poly-epitope specificity, single chain Abs, and fragments of Abs. A "monoclonal Ab" is obtained from a population of substantially homogeneous Abs, i.e., the individual Abs comprising the population are identical except for possible naturally-occurring mutations that may be present in minor amounts. Exemplary Abs include polyclonal (pAb), monoclonal (mAb), humanized, bi-specific (bsAb), and heteroconjugate Abs.

Polyclonal Abs can be raised in a mammalian host by one or more injections of an immunogen and, if desired, an adjuvant. Typically, the immunogen (and adjuvant) is injected in the mammal by multiple subcutaneous or intraperitoneal injections. Protocols for antibody production are well-known (Harlow and Lane, 1999).

Monoclonal antibodies may be prepared using hybridoma methods (Kohler and Milstein, 1976). Hybridoma methods comprise at least four steps: (1) immunizing a host, or lymphocytes from a host; (2) harvesting the mAb secreting (or potentially secreting) lymphocytes, (3) fusing the lymphocytes to immortalized cells, and (4) selecting those cells that secrete the desired mAb.

A rat, guinea pig, hamster, or other appropriate host is immunized to elicit lymphocytes that produce or are capable of producing Abs that will specifically bind to the immunogen. Alternatively, the lymphocytes may be immunized in vitro. If human cells are desired, peripheral blood lymphocytes (PBLs) are generally used; however, spleen cells or lymphocytes from other sources are preferred.

The lymphocytes are then fused with an immortalized cell line to form hybridoma cells, facilitated by a fusing agent such as polyethylene glycol. Rodent, bovine, or human myeloma cells immortalized by transformation may be used, or rat or mouse myeloma cell lines, and pure populations of hybridoma cells selected by well-known methods. The cells are tested for secreting antibodies that specifically bind the antigen of interest.

Monoclonal Abs may also be made by recombinant methods. DNA encoding the desired mAbs can be readily isolated and sequenced using conventional procedures, e.g., using oligonucleotide probes that specifically bind to murine heavy and light antibody chain genes, to probe preferably DNA isolated from secreting mAb hybridoma cell lines. Once isolated, the isolated DNA fragments are sub-cloned into expression vectors that are then transfected into host cells to express mAbs. The isolated DNA fragments can be modified by substituting the coding sequence for human heavy and light chain constant domains in place of the homologous murine sequences, or by fusing the Ig coding sequence to all or part of the coding sequence for a non-Ig polypeptide. Such a non-Ig polypeptide can be substituted for the constant domains of an antibody, or can be substituted for the variable domains of one antigen-combining site to create a chimeric bivalent antibody.

Antibodies may be monovalent Abs. One method of production involves recombinant expression of Ig light chain and modified heavy chain. Heavy chain truncations generally at any point in the Fc region will prevent heavy chain cross-linking. Alternatively, the relevant cysteine residues are substituted with another amino acid residue or are deleted, preventing crosslinking by disulfide binding. In vitro methods are also suitable for preparing monovalent Abs. Abs can be digested to produce fragments, such as Fab (Harlow and Lane, 1999).

Humanized forms of non-human Abs that bind a target molecule are chimeric Igs, Ig chains or fragments (such as Fv, Fab, Fab', F(ab')2 or other antigen-binding subsequences of Abs) that contain minimal sequence derived from non-human Ig.

Generally, a humanized antibody has one or more amino acid residues introduced from a non-human source. These non-human amino acid residues are often referred to as "import" residues, which are typically taken from an "import" variable domain. Humanization is accomplished by substituting rodent CDRs or CDR sequences for the corresponding sequences of a human antibody. Such "humanized" Abs are chimeric Abs, wherein substantially less than an intact human variable domain has been substituted by the corresponding sequence from a non-human species. Human Abs can also be produced using various techniques, including phage display libraries and human mAbs.

Human Abs can also be produced using various techniques, including phage display libraries (Hoogenboom et al., 1991; Marks et al., 1991) and human mAbs (Boerner et al., 1991; Reisfeld and Sell, 1985). Introducing human Ig genes into transgenic animals in which the endogenous Ig genes have been partially or completely inactivated can be exploited to synthesize human Abs. Upon challenge, human antibody production is observed, which closely resembles that seen in humans in all respects, including gene rearrangement, assembly, and antibody repertoire (U.S. Pat. No. 5,545,807, 1996; U.S. Pat. No. 5,569,825, 1996; U.S. Pat. No. 5,633,425, 1997; U.S. Pat. No. 5,661,016, 1997; U.S. Pat. No. 5,625,126, 1997; Fishwild et al., 1996; Lonberg and Huszar, 1995; Lonberg et al., 1994; Marks et al., 1992).

Bi-specific Abs are monoclonal that have binding specificities for at least two different antigens. The recombinant production of bi-specific Abs is often achieved by co-expressing two Ig heavy-chain/light-chain pairs, each having different specificities. The random assortment of these Ig heavy and light chains in the resulting hybridomas (quadromas) produce a potential mixture of ten different antibody molecules, of which only one has the desired bi-specific structure. The desired antibody can be purified using affinity chromatography or other techniques.

According to another aspect, the present invention further provides antibody alternatives or other binding molecules, such as soluble receptors, adnectins, peptides, peptide mimetics, small molecules, aptamers, major histocompatibility complex molecules etc., that exhibit binding specificity for a target molecule.

A binding molecule is said to "specifically bind" to a target molecule if it reacts at a detectable level (within, for example, an ELISA assay) with the target molecule (also referred to herein as the "agent") and does not react detectably in a statistically significant manner with unrelated molecules under similar conditions.

The term "peptide" refers to relatively short polypeptides, including peptides that consist of about 2, 3, 4, 5, 6, 7, 8, 9, 10, 11, 12, 13, 14, 15, 16, 17, 18, 19, 20, 25, 30, 35, 40, 45, or 50 amino acids, including all integers and ranges (e.g., 5-10, 8-12, 10-15) in between, and interact with a target molecule. Peptides can be composed of naturally-occurring amino acids and/or non-naturally occurring amino acids.

In addition to peptides consisting only of naturally-occurring amino acids, peptidomimetics or peptide analogs can also be used. A peptidomimetic is a molecule that mimics the biological activity of a peptide but is no longer peptidic in chemical nature.

Peptoid derivatives of peptides represent another form of modified peptides that retain the important structural determinants for biological activity, yet eliminate the peptide bonds, thereby conferring resistance to proteolysis (Simon et al., 1992). Peptoids are oligomers of N-substituted glycines. A number of N-alkyl groups have been described, each corresponding to the side chain of a natural amino acid.

A binding molecule may also include one or more small molecules. A "small molecule" refers to an organic compound that is of synthetic or biological origin, but is typically not a polymer. Organic compounds refer to a large class of chemical compounds which molecules contain carbon, typically excluding those that contain only carbonates, simple oxides of carbon, or cyanides. A "biomolecule" refers generally to an organic molecule that is produced by a living organism, including large polymeric molecules (biopolymers) such as peptides, polysaccharides, and nucleic acids as well, and small molecules such as primary secondary metabolites, lipids, phospholipids, glycolipids, sterols, glycerolipids, vitamins, and hormones. A "polymer" refers generally to a large molecule or macromolecule composed of repeating structural units, which are typically connected by covalent chemical bond.

In certain embodiments, a small molecule has a molecular weight of less than 1000-2000 Daltons, typically between about 300 and 700 Daltons, and including about 50, 100, 150, 200, 250, 300, 350, 400, 450, 500, 550, 500, 650, 600, 750, 700, 850, 800, 950, 1000 or 2000 Daltons.

Aptamers are also included as binding molecules (Ellington and Szostak, 1990; Tuerk and Gold, 1990). Examples of aptamers included nucleic acid aptamers (e.g., DNA aptamers, RNA aptamers) and peptide aptamers. Nucleic acid aptamers refer generally to nucleic acid species that have been engineered through repeated rounds of in vitro selection or equivalent method, such as SELEX (systematic evolution of ligands by exponential enrichment), to bind to various molecular targets such as small molecules, proteins, nucleic acids, and even cells, tissues and organisms.

Peptide aptamers typically include a variable peptide loop attached at both ends to a protein scaffold, a double structural constraint that typically increases the binding affinity of the peptide aptamer to levels comparable to that of an antibody's (e.g., in the nanomolar range. The variable loop length may be composed of about 10-20 amino acids, and the scaffold may include any protein that has good solubility and compacity properties. Peptide aptamer selection can be performed using different systems known in the art, including the yeast two-hybrid system.

Major histocompatibility complex (MHC) molecules play a key role in the immune system of animals. MHC molecules enable T cells to recognize antigens. There are three types of MHC molecules, class I, class II and class III. Class I and class II MHC molecules are glycoproteins that are present on the surface of the cell, while class III molecules are usually soluble molecules found intracellularly.

Binding targets are chosen by the application for the substrate-embedded hydrogel. For example, in the case of tumor treatment, targets are those that result in immune-mediate suppression and potential regression of tumor growth and include transforming growth factor beta (TGF-β), vascular endothelial growth factor A and C (VEGF-A and VEGF-C), chemokine (C-X-C motif) ligand 12 (CXCL12), interleukin 1 (IL-1), interleukin 8 (IL-8), interleukin 10 (IL-10), interleukin 17 (IL-17), TIMP metallopeptidase inhibitor 2 (TIMP2), fibroblast activation protein-α (FAP), chemokine (C-C motif) ligand 17 (CCL17), chemokine (C-C motif) ligand 21 (CCL21), hepatocyte growth factor (HGF), epidermal growth factor (EGF), basic fibroblast growth factor (bFGF), B-cell lymphoma 2 (bcl-2), interferon α (IFN-α), ligands of the natural killer group 2, member D (NKG2D) receptor including MICA, MICB, ULBP1, ULBP2, ULBP3, and ULBP4-6.

In the case of wound healing, target molecules can include ligands of the natural killer group 2, member D (NKG2D) receptor including MICA, MICB, ULBP1, ULBP2, ULBP3, and ULBP4-6; transforming growth factor α (TGF-α), transforming growth factor beta (TGF-β), interleukin 1 (IL-1), interleukin 6 (IL-6), interleukin 8 (IL-8), fibroblast growth factor 2, 7, and 10 (FGF-2, FGF-7, FGF-10), platelet derived growth factor (PDGF), tumor necrosis factor α (TNF-α), chemokine (C-X-C motif) ligand 10 (CXCL10), interferon γ (IFN-γ), angiostatin.

In other embodiments, the target molecule is a target analyte. In other embodiments, the target molecule is a contaminant in a sample that interferes with the detection or analysis of an analyte or agent. Yet in other embodiments, the binding target is a nucleoside/tide.

Targets can themselves be polypeptides, polypeptide fragments, lipids, such as glycolipids; sugars, organic molecules and inorganic molecules. In some embodiments, the target is a cell, which can be either a prokaryote or a eukaryote. In yet other embodiments, the target is a virus or viral particle.

The limitation of the selection of a binding target is the availability, or ability to make, a binding molecule that binds the desired target.

To detect a bound agent in the hydrogel, an intact hydrogel can be exposed to different disruption techniques such as heat shock and acid shock. In the case of heat shock, the hydrogel is exposed to a temperature that causes bound agents to release from the substrates. The temperature range for heat shock of bound agents is about 40° C. to 125° C., including 45° C. to 95° C. In the case of acid shock, the hydrogel is placed in an acid with a pH of 2, up to a pH of 6. After the heat shock or acid shock is performed, the bound agents are liberated into solution.

Heat shock and acid shock can also be performed after first separating from the hydrogel the plurality of substrates having the bound molecules. To physically liberate the substrates, the hydrogel can be physically disrupted through the use of mechanical agitation such as mashing or crushing the hydrogel with blunt implements such as a shaft or beads or through the use of sonication. The substrates can then be separated from the broken-up hydrogel with a magnetic field in the case of magnetic substrates or filtration or sedimentation in the case of all other substrates.

In the example of an alginate hydrogel, the hydrogel can be dissolved through exposure to a chelating agent such as ethylenediaminetetraacetic acid (EDTA) that will bind out the divalent ions, such as calcium, that are needed to form the gel.

In the example of an agarose hydrogel, the hydrogel can be dissolved through exposure to high heat that will cause the agarose to go back in solution.

The choice of removing substrates from a hydrogel or leaving them intact is in part dictated by downstream detection considerations. In the example where a bound agent is bound in the hydrogel in low abundance, it may be beneficial to first separate the substrates from the hydrogel and liberate (effectively elute) them into a small volume of liquid so that the available concentration of the agent is effectively higher for detection. In the example where a bound agent is bound in the hydrogel in high abundance, the hydrogel can be kept intact and the bound agents liberated (eluted) into a larger volume of liquid.

The choice of disruption techniques to liberate the bound agent from substrates is dictated in part on the type of interaction between the substrate and the agent. For example, acid or high heat may denature/partially denature an antibody and its bound antigen. Selection of the appropriate removal method is within the skill of one in the art.

Once liberated from the hydrogel, the bound agent can be detected by any means known to one of skill in the art. If the agent is a polypeptide, the polypeptide can be detected by Western blots, ELISA, or lateral flow detection. If the bound molecule is a nucleic acid, then amplification techniques, such as PCR, can be used, which products can be detected in a gel or in real time. These methods are all well-known to one of skill in the art.

Applications

Some of the applications of the invention are described below. These examples are not meant to limit the invention.

In some embodiments, the invention can be applied to an aqueous sample, wherein the binding molecule binds an analyte (agent) or a contaminant. The sample is contacted with the substrate-embedded hydrogel wherein the substrate is coated with binding molecules that bind (preferably specifically) the analyte or contaminant, and the analyte or contaminant is allowed to diffuse into the hydrogel and be bound by the binding molecule. To recover the analyte, for example, the hydrogel is removed from the sample. In the case of removing a contaminant from a sample, the gel may be left in the sample, which is then further analyzed, or the gel is removed from the sample.

In some embodiments, the analyte is a molecule that is correlated with a disease or disorder. A sample from a subject is contacted with a substrate-embedded hydrogel wherein the binding molecule binds the analyte, usually a polypeptide, which presence is correlated with the disease or disorder. The analyte is then analyzed and/or quantified. As a non-limiting example, Table 2 gives examples of cancer markers that can be used in embodiments of the invention.

TABLE 2

Tumor markers and associated tumor types
(Adapted from Casciato and Territo (Casciato and Territo, 2009))

| Tumor marker | Associated tumor types |
|---|---|
| Alpha fetoprotein (AFP) | germ cell tumor, hepatocellular carcinoma |
| Calretinin | mesothelioma, sex cord-gonadal stromal tumour, adrenocortical carcinoma, synovial sarcoma |
| Carcinoembryonic antigen | gastrointestinal cancer, cervix cancer, lung cancer, ovarian cancer, breast cancer, urinary tract cancer |
| CD34 | hemangiopericytoma/solitary fibrous tumor, pleomorphic lipoma, gastrointestinal stromal tumor, dermatofibrosarcoma protuberans |

TABLE 2-continued

Tumor markers and associated tumor types
(Adapted from Casciato and Territo (Casciato and Territo, 2009))

| Tumor marker | Associated tumor types |
| --- | --- |
| CD99MIC 2 | Ewing sarcoma, primitive neuroectodermal tumor, hemangiopericytoma/solitary fibrous tumor, synovial sarcoma, lymphoma, leukemia, sex cord-gonadal stromal tumour |
| CD117 | gastrointestinal stromal tumor, mastocytosis, seminoma |
| Chromogranin | neuroendocrine tumor |
| Cytokeratin (various types) | Many types of carcinoma, some types of sarcoma |
| Desmin | smooth muscle sarcoma, skeletal muscle sarcoma, endometrial stromal sarcoma |
| Epithelial membrane antigen (EMA) | many types of carcinoma, meningioma, some types of sarcoma |
| Factor VIII, CD31 FL1 | vascular sarcoma |
| Glial fibrillary acidic protein (GFAP) | glioma (astrocytoma, ependymoma) |
| Gross cystic disease fluid protein(GCDFP-15) | breast cancer, ovarian cancer, salivary gland cancer |
| HMB-45 | melanoma, PEComa (for example angiomyolipoma), clear cell carcinoma, adrenocortical carcinoma |
| Human chorionic gonadotropin (hCG) | gestational trophoblastic disease, germ cell tumor, choriocarcinoma |
| immunoglobulin | lymphoma, leukemia |
| inhibin | sex cord-gonadal stromal tumour, adrenocortical carcinoma, hemangioblastoma |
| keratin (various types) | carcinoma, some types of sarcoma |
| lymphocyte marker (various types | lymphoma, leukemia |
| MART-1 (Melan-A) | melanoma, steroid-producing tumors (adrenocortical carcinoma, gonadal tumor) |
| Myo D1 | rhabdomyosarcoma, small, round, blue cell tumour |
| muscle-specific actin (MSA) | myosarcoma (leiomyosarcoma, rhabdomyosarcoma) |
| neurofilament | neuroendocrine tumor, small-cell carcinoma of the lung |
| neuron-specific enolase (NSE) | neuroendocrine tumor, small-cell carcinoma of the lung, breast cancer |
| placental alkaline phosphatase (PLAP) | seminoma, dysgerminoma, embryonal carcinoma |
| prostate-specific antigen | prostate |
| PTPRC (CD45) | lymphoma, leukemia, histiocytic tumor |
| S100 protein | melanoma, sarcoma (neurosarcoma, lipoma, chondrosarcoma), astrocytoma, gastrointestinal stromal tumor, salivary gland cancer, some types of adenocarcinoma, histiocytic tumor(dendritic cell, macrophage) |
| smooth muscle actin (SMA) | gastrointestinal stromal tumor, leiomyosarcoma, PEComa |
| synaptophysin | neuroendocrine tumor |
| thyroglobulin | post-operative marker of thyroid cancer (but not in medullary thyroid cancer) |
| thyroid transcription factor-1 | all types of thyroid cancer, lung cancer |
| vimentin | sarcoma, renal cell carcinoma, endometrial cancer, lung carcinoma, lymphoma, leukemia, melanoma |

In another embodiment, the invention can be applied to enhance wound and tissue trauma healing. In such embodiments, the substrate-embedded hydrogel, wherein the substrates are coated with binding molecules that bind desired target molecules that when removed from a wound or trauma site, allow healing to be accelerated, such as those molecules disclosed above, is applied to the wound or trauma, or in proximity to the wound or trauma, and allowed to heal. The hydrogel may be replaced at intervals so that unbound binding molecules are consistently available so as to continuously facilitate the desired physiological response over a course of time.

In yet another embodiment, the invention can be applied to treat tumors. In such embodiments, the substrate-embedded hydrogel has a plurality of substrates loaded with binding molecules known to have anti-tumor activity, such as those listed above. The hydrogel is applied in proximity to or directly contacting the tumor, and if possible, changed at regular intervals so that unbound binding molecules are consistently available so as to continuously facilitate physiological responses adverse to a tumor cell, particularly growth and maintenance of the tumor cell, and the tumor cell microenvironment.

Kits

Kits, containers, packs, or dispensers containing substrate-embedded hydrogels, together with instructions for administration, may be assembled. When supplied as a kit, the different components may be packaged in separate containers and admixed immediately before use, such as the components of the packaged hydrogel. Such packaging of the components separately may permit long-term storage without losing active component functions.

Kits may also include reagents in separate containers that facilitate the execution of a specific test, such as diagnostic tests. The components of a kit are a substrate-embedded hydrogel prepared to bind a target molecule, a control sample, and optionally a composition to detect the bound target molecule or agent. Control components may include: a sample containing the target molecule, and a sample not containing the target molecule. Other components may include buffers, fixatives, blocking solutions; detergent or detergent solutions or other permeabilizing reagents; miscellaneous reagents, protease inhibitors, various containers and miscellaneous tools and equipment to facilitate the assays.

In many cases, especially convenient kits may be assembled not only with the components listed above, but also with means for collecting a sample.

(a) Containers or Vessels

Reagents included in kits can be supplied in containers of any sort such that the life of the different components are preserved and are not adsorbed or altered by the materials of the container. For example, sealed glass ampules may contain lyophilized hydrogels, or hydrogel components, or buffers that have been packaged under a neutral, non-reacting gas, such as nitrogen. Ampules may consist of any suitable material, such as glass, organic polymers (i.e., polycarbonate, polystyrene, etc.), ceramic, metal or any other material typically employed to hold reagents. Other examples of suitable containers include simple bottles that may be fabricated from similar substances as ampules, and envelopes that may have foil-lined interiors, such as aluminum or alloy. Other containers include test tubes, vials, flasks, bottles, syringes, or the like. Containers may have a sterile access port, such as a bottle having a stopper that can be pierced by a hypodermic injection needle. Other containers may have two compartments that are separated by a readily removable or rupturable membrane that upon removal or rupture permits the components to mix. Removable membranes may be glass, plastic, rubber, etc.

(b) Instructional Materials

Kits may also be supplied with instructional materials. Instructions may be printed on paper or other substrate and/or may be supplied as an electronic-readable medium, such as a floppy disc, CD-ROM, DVD-ROM, DVD, videotape, audio tape, etc. Detailed instructions may not be physically associated with the kit; instead, a user may be directed to an internet web site specified by the manufacturer or distributor of the kit, or supplied as electronic mail.

EXAMPLES

The following examples are given to exemplify the invention, not to limit it in any way.

Example 1: Chitosan/PEI Gel

For generation of chitosan/PEI hydrogel, the polysaccharide chitosan is prepared to have over 75% deacetylation (Sigma Aldrich; St. Louis, Mo.) and dissolved in 1% acetic acid for 24 hours at a concentration of 1.0% (w/v) then autoclaved. To this chitosan solution is mixed one part of the linear-branch cationic polymer PEI (Sigma) at a concentration of 10% (v/v) with an average molecular weight of 25,000 to four parts chitosan solution. Diluted in the linear-branch cationic polymer-PEI solution are sub-micron polystyrene beads with an average diameter of 800 nanometers (Spherotech, Inc.; Lake Forest, Ill.) at a concentration of 1% (w/v). These polystyrene beads are attached to monoclonal antibodies (α-fluorescein isothiocyanate (FITC); Sigma) that are covalently reacted against the surface chemistry of the polystyrene beads. The polymerization reaction proceeds for a minimum of 1 minute and ideally 5 minutes. Upon polymerization of the gel, the polystyrene beads are embedded within the microporous matrix of the gel.

This gel with embedded substrates can then be placed in a buffered aqueous sample containing a target molecule recognized by the antibody attached to the polystyrene beads for a minimum of 1 minute.

Example 2: Chitosan/Glycerol Phosphate Gel

Chitosan is prepared to have over 75% deacetylation (Sigma) and dissolved in 1% acetic acid for 24 hours at a concentration of 1.0% (w/v) then autoclaved. To this chitosan solution is mixed an equal part of with one part 40% (w/v) glycerol phosphate (Sigma) containing 800 nanometer polystyrene beads (Spherotech) coated with monoclonal antibodies (α-FITC; Sigma). The mixture forms a gel at about 37° C.

Example 3: Chitosan/Poly(Ethylene Oxide) Gel

Chitosan is prepared to have over 75% deacetylation (Sigma) and dissolved in 1% acetic acid (Sigma) for 24 hours at a concentration of 1.0% (w/v) then autoclaved. To this chitosan solution is mixed an equal volume of 1.5% (w/v) poly(ethylene oxide) (Sigma) containing 800 nm polystyrene beads (Spherotech) coated with monoclonal antibodies (α-FITC; Sigma). Gel is allowed to form for at least 4 hours at room temperature.

Example 4: Low-Melting Point Agarose Gel

Low melting point (LMP)-agarose (Sigma) is added at a concentration of 1% (w/v) in a PBS buffer and heated until the LMP agarose dissolves in solution. The resulting LMP agarose solution is reduced in temperature to 35° C. in a water bath. To form the gel, one part LMP agarose solution is mixed with an equal part of PBS solution kept at room temperature (23° C.) containing 1% (w/v) sub-micron polystyrene beads with an average diameter of 800 nanometers (Spherotech), which surfaces are coated with monoclonal antibodies (α-FITC, Sigma). After at least 15 seconds of mixing, the hydrogel is formed.

Example 5: Alginate Gel

The anionic polysaccharide alginic acid (alginate) (Sigma) is dissolved in water at 5% (w/v) then autoclaved and mixed. A ratio of 4:1 of 5% (w/v) alginate is mixed with 4 Molar $CaCl_2$ solution containing 1% (w/v) sub-micron polystyrene beads with an average diameter of 800 nanometers, whose surfaces are coated with monoclonal antibodies. The two parts are mixed for at least 5 seconds and a gel with embedded substrates is formed. The hydrogel resulting from this formulation is nearly identical to texture to the chitosan/PEI gel (Example 1) except it is more resistant to fragmentation, and it re-assumes its initial smooth, spherical shape after deformation caused by pressing on it bluntly.

Figure 3:
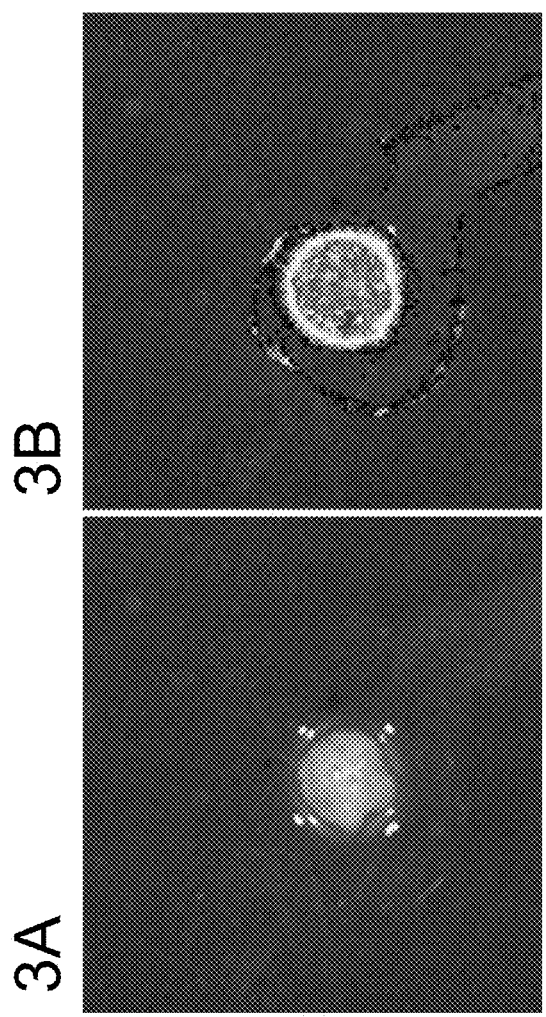
FIG. 3 shows the results of an experiment demonstrating the absorption of a target molecule by a hydrogel of the invention.

Example 6: Demonstration of Binding Out of a Substance Using a Substrate-Embedded Hydrogel A chitosan/PEI hydrogel was prepared according to Example 1. The embedded substrates were coated with monoclonal mouse IgG (Sigma) that recognizes and binds to FITC. In this case, the FITC was covalently linked to streptavidin protein, with 3-9 FITC molecules per streptavidin. A test tube containing 1 mL of a 1 µM solution of the FITC-labelled streptavidin protein (Sigma) was prepared in phosphate buffered saline (PBS), to which was added a 200 µL preparation of the hydrogel. After 3 minutes of co-incubation of the hydrogel in the FITC-labelled streptavidin solution, the hydrogel was removed from the test tube with tweezers and placed on a plastic dish. The dish was then placed under a microscope and first illuminated overhead with white light and photographed (FIG. 3A), then excited from overhead at 488 nm and the fluorescence imaged at 518 nm (FIG. 3B). The fluorescence image demonstrated that a large amount of the FITC-labelled streptavidin substrate was efficiently absorbed and concentrated in the hydrogel. The slight fluorescent halo seen around the hydrogel is most likely due to the coffee ring effect whereby molecules flow to a droplet's edge as the solution evaporates.

Those skilled in the art will recognize, or be able to ascertain using no more than routine experimentation, many equivalents to the specific embodiments of the invention described herein. Where any concept(s) or element(s) of the invention is separately presented for convenience, it is understood that the combination of any such separately presented concept(s) or element(s), as necessary, is also encompassed by the invention. Such equivalents are intended to be encompassed by the claims.

The contents of the patents and references cited throughout this specification are hereby incorporated by reference in their entireties.

REFERENCES

Annabi, N., S. M. Mithieux, E. A. Boughton, A. J. Ruys, A. S. Weiss, and F. Dehghani. 2009. Synthesis of highly porous crosslinked elastin hydrogels and their interaction with fibroblasts in vitro. *Biomaterials.* 30:4550-4557.

Annabi, N., S. M. Mithieux, P. Zorlutuna, G. Camci-Unal, A. S. Weiss, and A. Khademhosseini. 2013. Engineered cell-laden human protein-based elastomer. *Biomaterials.* 34:5496-5505.

Annabi, N., J. W. Nichol, X. Zhong, C. Ji, S. Koshy, A. Khademhosseini, and F. Dehghani. 2010. Controlling the porosity and microarchitecture of hydrogels for tissue engineering. *Tissue engineering. Part B, Reviews.* 16:371-383.

Annabi, N., A. Tamayol, J. A. Uquillas, M. Akbari, L. E. Bertassoni, C. Cha, G. Camci-Unal, M. R. Dokmeci, N. A. Peppas, and A. Khademhosseini. 2014. 25th anniversary article: Rational design and applications of hydrogels in regenerative medicine. *Advanced materials.* 26:85-123.

Baruch, L., and M. Machluf. 2006. Alginate-chitosan complex coacervation for cell encapsulation: effect on mechanical properties and on long-term viability. *Biopolymers.* 82:570-579.

Berger, J., M. Reist, J. M. Mayer, O. Felt, N. A. Peppas, and R. Gurny. 2004. Structure and interactions in covalently and ionically crosslinked chitosan hydrogels for biomedical applications. *European journal of pharmaceutics and biopharmaceutics: official journal of Arbeitsgemeinschaft fur Pharmazeutische Verfahrenstechnik e. V.* 57:19-34.

Boddu, V., and E. Smith. 2004. COOMPOSITE BIOSORBENT FOR TREATMENT OF WASTE AQUEOUS SYSTEM(S) CONTAINING HEAVY METALS. U.S. Pat. No. 6,786,336.

Casciato, D. A., and M. C. Territo. 2009. Manual of clinical oncology. Lippincott Williams & Wilkins, Philadelphia. p. pp.

DiCosmo, F., and V. DiTizio. 2001. DRUG DELIVERY VIA THERAPEUTIC HYDROGELS. U.S. Pat. No. 6,228,393.

Djonlagic, J., D. Zugic, and Z. Petrovic. 2012. High Strength Thermoresponsive Semi-IPN Hydrogels Reinforced with Nano-clays. *J Appl Polym Sci.* 124:3024-3036.

Ellington, A. D., and J. W. Szostak. 1990. In vitro selection of RNA molecules that bind specific ligands. *Nature.* 346:818-822.

Gong, J. 2010. Why are double network hydrogels so tough? *Soft Matter.* 6:2583-2590.

Hagiwara, K., H. Kitoh, Y. Oshibe, and H. Ohmura. 1996. MEDICAL INSTRUMENT. U.S. Pat. No. 5,582,794.

Hahn, M. S., B. A. Teply, M. M. Stevens, S. M. Zeitels, and R. Langer. 2006. Collagen composite hydrogels for vocal fold lamina propria restoration. *Biomaterials.* 27:1104-1109.

Hague, M., T. Kurokawa, G. Kamita, and J. Gong. 2011. Lamellar bilayers as reversible sacrificial bonds to toughen hydrogel: hysteresis, self-recovery, fatigue resistance, and crack blunting. *Macromolecules.* 44:8916-8924.

Haraguchi, K., and T. Takehisa. 2002. Nanocomposite hydrogels: a unique organic-inorganic network structure with extraordinary mechanical, optical, and swelling/de-swelling properties. *Adv. Mater.* 14:1120-1124.

Harlow, E., and D. Lane. 1999. Using antibodies: a laboratory manual. Cold Spring Harbor Laboratory Press, Cold Spring Harbor, N.Y. xiv, 495 p. pp.

Harris, J., and S. Hajela. 2015. CHITOSAN BASED ADSORBENT. U.S. Pat. No. 8,932,983.

Hua, S., H. Ma, X. Li, H. Yang, and A. Wang. 2010. pH-sensitive sodium alginate/poly(vinyl alcohol) hydrogel beads prepared by combined $Ca^{2+}$ crosslinking and freeze-thawing cycles for controlled release of diclofenac sodium. *International journal of biological macromolecules.* 46:517-523.

Kistler, S. 1931. Coherent expoanded aerogels and jellies. *Nature.* 127:741.

Kohler, G., and C. Milstein. 1976. Derivation of specific antibody-producing tissue culture and tumor lines by cell fusion. *European journal of immunology.* 6:511-519.

Leach, J. B., J. B. Wolinsky, P. J. Stone, and J. Y. Wong. 2005. Crosslinked alpha-elastin biomaterials: towards a processable elastin mimetic scaffold. *Acta biomaterialia.* 1:155-164.

Lee, K. Y., and D. J. Mooney. 2001. Hydrogels for tissue engineering. *Chemical reviews.* 101:1869-1879.

Li, Y., J. Rodrigues, and H. Tomas. 2012. Injectable and biodegradable hydrogels: gelation, biodegradation and biomedical applications. *Chemical Society reviews.* 41:2193-2221.

MacEwan, S. R., and A. Chilkoti. 2010. Elastin-like polypeptides: biomedical applications of tunable biopolymers. *Biopolymers.* 94:60-77.

Moro, D., G. Griffin, and M. Andrea. 1981. PLASTIC WOUND BANDAGE. U.S. Pat. No. 4,272,518.

Moro, D., P. Kuzma, and H. Quandt. 1994. MANUFACTURE OF WATER-SWELLABLE HYDROPHILIC ARTICLES AND DRUG DELIVERY DEVICES. U.S. Pat. No. 5,292,515.

Myung, D., D. Waters, M. Wiseman, P. E. Duhamel, J. Noolandi, C. N. Ta, and C. W. Frank. 2008. Progress in the development of interpenetrating polymer network hydrogels. *Polymers for advanced technologies.* 19:647-657.

Okumura, Y., and K. Ito. 2001. The Polyrotaxane Gel: A Topological Gel by Figure-of-Eight Cross-links. *Advanced materials.* 13:485-487.

Patel, A., A. K. Gaharwar, G. Iviglia, H. Zhang, S. Mukundan, S. M. Mihaila, D. Demarchi, and A. Khademhosseini. 2013. Highly elastomeric poly(glycerol sebacate)-co-poly(ethylene glycol) amphiphilic block copolymers. *Biomaterials.* 34:3970-3983.

Sawhney, A. S., C. P. Pathak, and J. A. Hubbell. 1993. Interfacial photopolymerization of poly(ethylene glycol)-based hydrogels upon alginate-poly(l-lysine) microcapsules for enhanced biocompatibility. *Biomaterials.* 14:1008-1016.

Shi, R., D. Chen, Q. Liu, Y. Wu, X. Xu, L. Zhang, and W. Tian. 2009. Recent advances in synthetic bioelastomers. *International journal of molecular sciences.* 10:4223-4256.

Simon, R. J., R. S. Kania, R. N. Zuckermann, V. D. Huebner, D. A. Jewell, S. Banville, S. Ng, L. Wang, S. Rosenberg, C. K. Marlowe, and et al. 1992. Peptoids: a modular approach to drug discovery. *Proceedings of the National Academy of Sciences of the United States of America.* 89:9367-9371.

St. John, J., and D. Moro. 2011. HYDROGEL WOUND DRESSING AND BIOMATERIALS FORMED IN SITU AND THEIR USES. U.S. Pat. No. 7,910,135.

Sun, J. Y., X. Zhao, W. R. Illeperuma, O. Chaudhuri, K. H. Oh, D. J. Mooney, J. J. Vlassak, and Z. Suo. 2012. Highly stretchable and tough hydrogels. *Nature.* 489:133-136.

Teng, D. 2012. From chitin to chitosan. In Chitosan-based hydrogels. K. Yao, J. Li, F. Yao, and Y. Yin, editors. CRC Press—Taylor & Francis Group, Boca Rotan, Fla. 1-37.

Thomas, D., and L. Sperling. 1978. Interpenetrating polymer networks. Academic Press, New York, N.Y.

Tuerk, C., and L. Gold. 1990. Systematic evolution of ligands by exponential enrichment: RNA ligands to bacteriophage T4 DNA polymerase. *Science.* 249:505-510.

van Eldijk, M. B., C. L. McGann, K. L. Kiick, and J. C. van Hest. 2012. Elastomeric polypeptides. *Topics in current chemistry.* 310:71-116.

Wang, Q., J. Zhang, and A. Wang. 2009. Preparation and characterization of a novel pH-sensitive chitosan-g-poly (acrylic acid)/attapulgite/sodium alginate composite hydrogel bead for controlled release of diclofenac sodium. *Carbohyd Polym.* 78:731-737.

Wang, Y., G. A. Ameer, B. J. Sheppard, and R. Langer. 2002. A tough biodegradable elastomer. *Nature biotechnology.* 20:602-606.

I claim:

1. A biocompatible hydrogel comprising an organic polymer, wherein embedded within the biocompatible hydrogel is a plurality of substrates, and wherein the plurality of substrates comprises at least one binding molecule immobilized on each substrate, wherein the organic polymer poly(ethylenimine) is present at about 0.5% (v/v) to about 3.3% (v/v) and the chitosan is present at about 0.45% (w/v) to about 2.4% (w/v).

2. The biocompatible hydrogel of claim 1, wherein the poly(ethylenimine) is present at about 2% (v/v) and the chitosan is present at about 0.8% (w/v).

3. The biocompatible hydrogel of claim 1, wherein each substrate comprises one selected from the group consisting of agarose, cross-linked agarose, cellulose, dextran, polyacrylamide, latex, polystyrene, polyethylene, polypropylene, polyfluoroethylene, polyethyleneoxy, glass, silica, controlled pore glass, reverse phase silica, and metal.

4. The biocompatible hydrogel of claim 3, wherein at least one substrate comprises polystyrene.

5. The biocompatible hydrogel of claim 3, wherein the plurality of substrates is present at about 0.01% (w/v) to about 1% (w/v).

6. The biocompatible hydrogel of claim 1, wherein each binding molecule is selected from the group consisting of a binding polypeptide, a binding nucleotide, a sugar, a binding polypeptide that binds at least one antigen, an antibody, an antibody fragment, an scFv molecule, a major histocompatibility complex molecule, and an aptamer.

7. A method of detecting an agent, comprising (a) contacting a sample with the biocompatible hydrogel of claim 1, and wherein the binding molecule binds an agent; (b) allowing the binding molecule to bind the agent; and (c) analyzing the biocompatible hydrogel for the presence of the agent.

8. A method of detecting a disease or disorder, comprising (a) providing a sample from a subject suspected of suspected of suffering from a disease or disorder; (b) contacting the sample with the biocompatible hydrogel of claim 1, wherein the binding molecule binds a molecule correlated with the presence of the disease or disorder; and (c) detecting from the biocompatible hydrogel the presence of the bound molecule.

9. A method for removing an agent from a sample, comprising (a) contacting a sample with the biocompatible hydrogel of claim 1, wherein the binding molecule binds an agent; (b) allowing the binding molecule to bind the agent; and (c) removing the biocompatible hydrogel from the sample, wherein removing the biocompatible hydrogel results in removing at least a quantity of the agent from the sample.

10. A method of treating a tumor cell, comprising placing in proximity to, or contacting, the tumor cell with the biocompatible hydrogel of claim 1, wherein the binding molecule binds a tumor-promoting factor.

11. The method of claim 10, wherein the tumor-promoting factor comprises at least one selected from the group consisting of transforming growth factor β, vascular endothelial growth factor A, vascular endothelial growth factor C, chemokine ligand 12, Interleukin 1, Interleukin 8, Interleukin 10, Interleukin 17, TIMP metallopeptidase inhibitor 2, fibroblast activation protein-α, chemokine ligand 17, chemokine ligand 21, hepatocyte growth factor, epidermal growth factor, basic fibroblast growth factor, B-cell lymphoma 2, interferon α, natural killer group 2 ligands, and a member D receptor.

12. A method of treating a wound or tissue trauma, comprising contacting the wound or tissue trauma with the biocompatible hydrogel of claim 1, wherein the binding molecule binds a healing-deterring factor.

13. The method of claim 12, wherein the healing-deterring factor is selected from the group consisting of natural killer group 2 ligands, member D, transforming growth factor α, transforming growth factor β, interleukin 1, interleukin 6, interleukin 8, fibroblast growth factor 2, fibroblast growth factor 7, fibroblast growth factor 10, platelet derived growth factor, tumor necrosis factor α, chemokine ligand 10, interferon γ, and angiostatin.

14. A kit, comprising instructions and components of a biocompatible hydrogel and a plurality of substrates comprising a binding molecule to be embedded therein, and at least one solvent, wherein the solvent, components, and the plurality of substrates are mixed before use, wherein the biocompatible hydrogel comprises an organic polymer which comprises poly(ethylenimine) and chitosan and wherein the poly(ethylenimine) is present at about 0.5% (v/v) to about 3.3% (v/v) and the chitosan is present at about 0.5% (w/v) to about 2.4% (w/v).

* * * * *